United States Patent [19]

Rosenberg

[11] Patent Number: 4,925,799

[45] Date of Patent: May 15, 1990

[54] PLASMID CLONING VECTOR PAS1

[75] Inventor: Martin Rosenberg, Malvern, Pa.

[73] Assignee: The United States of America as represented by the Department of Health and Human Services, Washington, D.C.

[21] Appl. No.: 819,406

[22] Filed: Jan. 16, 1986

Related U.S. Application Data

[63] Continuation-in-part of Ser. No. 457,352, Jan. 12, 1983, Pat. No. 4,578,355.

[51] Int. Cl.$^5$ .................. C12N 15/00; C12N 1/00
[52] U.S. Cl. .................. 435/172.3; 435/320; 935/29; 935/23
[58] Field of Search .................. 435/68, 172.3, 320; 935/11, 29

[56] References Cited

U.S. PATENT DOCUMENTS 4,578,355  3/1986  Rosenberg .................. 435/6 X

OTHER PUBLICATIONS

Rosenberg, M. et al., in *Methods in Enzymology*, vol. 101, pp. 123–138, 1983.

Morrow, J. in *Methods in Enzymology*, vol. 68, pp. 3–24, 1979.

Shatzman and Rosenberg, "A Plasmid Cloning Vector for Inducible Overproduction of Proteins in Bacterial Cells," Miami Symposium, Jan. 14, 1982, Abstract, p. 98.

Shimatake and Rosenberg, *Nature*, vol. 292, No. 5819, pp. 128–132, Jul. 9, 1981.

Lewin, *Gene Expression*-3, John Wiley, 1977, pp. 352, 355, 371.

Kornberg, DNA Replication, W. H. Freeman and Co., 1980, pp. 539–540.

Backman et al., *Cell*, 13:65–71, Jan. 1978.

Old et al., *Principles of Gene Manipulation*, 2d ed., Univ. of California Press, 1981, p. 35+.

*Primary Examiner*—Jayme A. Huleatt
*Attorney, Agent, or Firm*—Mishrilal Jain; John S. Roberts, Jr.

[57] ABSTRACT

A plasmid cloning vector containing both transcriptional and translational regulatory sequences derived from the bacteriophage lambda genome was constructed to achieve high level expression of prokaryotic and eukaryotic genes. The system utilizes a plasmid vehicle carrying the strong, regulatable lambda promoter, $P_L$, and host lysogens into which this vector can be stably transformed. The lysogen synthesizes sufficient repressor (cI) to control $P_L$ expression and thereby stabilize plasmids which carry such a highly efficient promoter. Use of a temperature sensitive repressor permits simple, rapid induction of $P_L$ transcripts at any given time. Efficient transcription of essentially any coding sequence is assured by providing the phage lambda antitermination factor, N, and a site on the transcription unit for its utilization (Nut site). This pAS1 plasmic closely resembles the earlier constructed pKC30cII, also a regulatory protein which activates promoters for lysogenic development.

11 Claims, 2 Drawing Sheets

PLASMID CLONING VECTOR PAS1

This application is a continuation-in-part of my copending application Ser. No. 06/457,352 filed Jan. 12, 1983, now U.S. Pat. No. 4,578,355, issued Mar. 25, 1986, entitled Plasmid Cloning Vector pAS1.

A plasmid cloning vector containing both transcriptional and translational regulatory sequences derived from the bacteriophage lambda genome was constructed to achieve high level expression of prokaryotic and eukaryotic genes.

The system utilizes a plasmid vehicle carrying the strong, regulatable lambda promoter, $P_L$, and host lysogens into which this vector can be stably transformed. The lysogen synthesizes sufficient repressor (cI) to control $P_L$ expression and thereby stabilize plasmids which carry such a highly efficient promoter. Use of a temperature sensitive repressor permits simple, rapid induction of $P_L$ transcripts at any given time. Efficient transcription of essentially any coding sequence is assured by providing the phage lambda antitermination factor, N, and a site on the transcription unit for its utilization (Nut site). This pAS1 plasmid closely resembles the earlier constructed pKC30cII. cII is a regulatory protein which activates promoters for lysogenic development.

This production of pAS1 was done by appropriately inserting into the $P_L$ transcription unit the ribosome binding site and initiation codon of the efficiently translated phage lambda cII gene. Immediately adjacent to the initiator ATG, there was engineered a unique cloning site which allows any coding sequence to be fused in frame directly to the cII start site. This system has been used to overproduce one prokaryotic (E. coli β galactosidase) and one eukaryotic (SV40 small T antigen) protein. β-galactosidase is synthesized as 30–40% of cell protein and small T as >5% of cell protein after only a 60–90 minute induction.

Expression of Eukaryotic Genes

Vector Construction. In order to extend the pKC30 system to the expression of genes lacking E. coli translational regulatory information, an efficient ribosome recognition and translation initiation site was engineered into the $P_L$ transcription unit. The site chosen was that of the efficiently translated λ phage gene, cII. The entire coding region of this gene was removed leaving only its initiator f-met codon and upstream regulatory sequences. Neither the sequence nor the position of any nucleotides in the ribosome binding region was altered. Instead, a restriction site for insertion of the desired gene was introduced immediately downstream from the ATG initiation codon. This was done by fusing the BamHI site of pBR322 directly to the cII ATG codon. This fusion retains the BamHI site and positions one side of the staggered cut immediately adjacent to the ATG codon permitting ready access to the cII translational regulatory information. The resulting vector, pAS1, allows direct fusion of any coding sequence (prokaryotic, eukaryotic, or synthetic) to the cII translational regulatory signal. Illustrative is the fusion of the lacZ gene shown post. Essentially, any gene can be adapted for insertion into the pAS1 vector and various examples are described below. Note that expression of genes cloned into pAS1 is controlled by temperature induction, exactly analogous to the pKC30 vector system.

Figure 2:
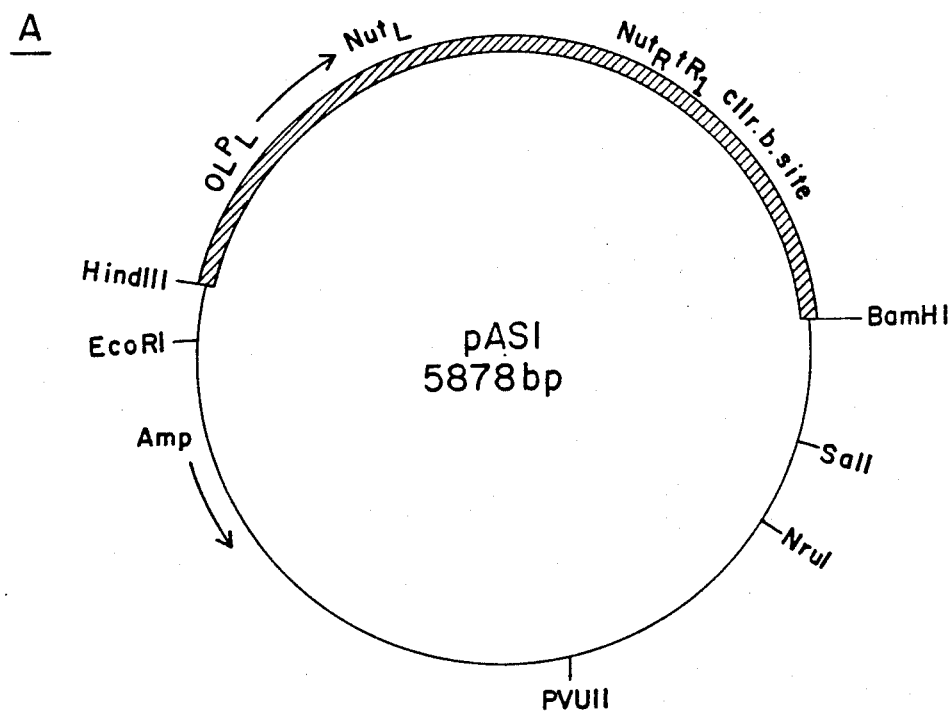
FIG. 2 is a partial genetic map of pAS1. Referring to the pKC30 system (derivative of pBR322) and pKC30c$^{TT}$ system noted above and described at FIG. 1, the following is described as the production of the vector construction of pAS1 from its parent, pKC30.
Figure 2:
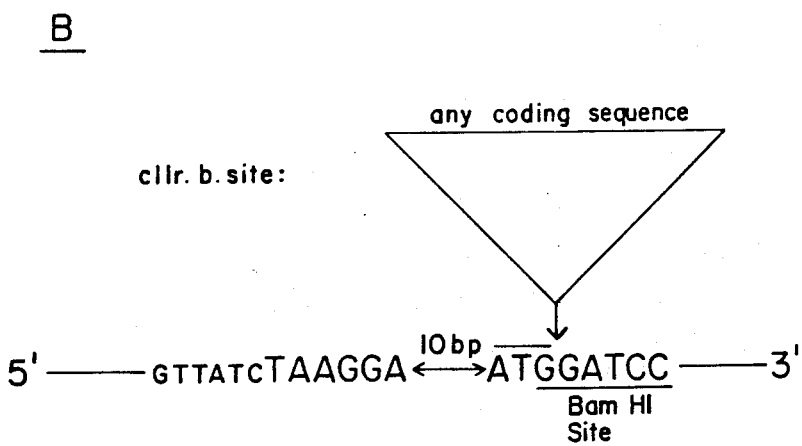

In other words, pAS1 is a plasmid vector capable of expressing a polypeptide comprising a plasmid having the $P_L$ promoter and Nut L site from pKC30 and, downstream of the Nut L site, the Nut R site, the tR1 site and the cII ribosome binding site including the cII translation initiation codon, from lambda DNA; immediately downstream of the cII ATG is a BamHI site, as illustrated in FIG. 2. The vector was constructed by inserting the lambda DNA between the HpaI and BamHI sites of pKC30. The lambda DNA had been previously mutationally altered such that the cII ribosome binding site could be fused to the BamHI site. The vector can be constructed from pKC30cII by cutting back the cII gene to the cII ATG, restricting the plasmid with BamHI, and regulating the plasmid. The vector can also be constructed by similarly cutting back the cII gene from lambda DNA, attaching a BamHI linker, and inserting the Nut R - cII ATG fragment into pKC30.

Expression of lacZ in pAS1. In order to test the ability of the cII ribosome binding site to direct translation of another gene, there was initially fused the *E. coli* lacZ gene to the cII ATG initiation codon. This was accomplished by using a lacZ gene construction into which a unique BamHI restriction site had been engineered near the 5'-end of the gene. Direct ligation of this BamHI site to the BamHI site in pAS1 created the appropriate in frame fusion of lacZ to the cII ATG codon. In this vector lacZ expression is controlled entirely by the transcriptional and translational signals provided on pAS1. The pAS1 lacZ construction results in high level expression of β-galactosidase. After only one hour of temperature induction, β-galactosidase accounts for 30–40% of total cellular protein.

Utility Statement

In addition to the utilities asserted in the abstract, it is noted that the present plasmid vector system may be utilized to achieve high level expression of particular phage regulatory protein which are normally found in only minute amounts in phage infected bacterial cells. The ease with which pAS1 vector may be used to fuse makes it commercially of great interest, particularly in regard to expressing polypeptides such as interferon, human growth hormone, and insulin.

Material Information Disclosure

Shatzman and Rosenberg, "A Plasmid Cloning Vector for Inducible Overproduction of Proteins in Bacterial Cells," Miami Symposium, Jan. 14, 1982, abstract, p. 98.

Shimatake and Rosenberg, "Purified λ Regulatory Protein cII Positively Activates Promoters for Lysogenic Development," Nature, Vol. 292, No. 5819, pp. 128–132, July 9, 1981.

Lewin, *Gene Expression*-3, John Wiley, 1977, Chapter 4 "Phage Lambda Infective Pathways," especially page 352 lysogeny and pages 355, 371 on turn off of repressor and cII gene.

Kornberg, *DNA Replication*, W. H. Freeman and Company, 1980, pp. 539–40, λ Temperate Phages.

Backman et al, "Maximizing Gene Expression on a Plasmid Using Recombination in Vitro," *Cell*, 13:65–71, January 1978—background information on ribosome binding sites (rbs).

Old et al, *Principles of Gene Manipulation*, 2d ed., University of California Press, 1981, pages 35+, re pBR322.

Source

The description and production of the parent cII gene is described fully in the *Nature* article above (1981).

The conversion from cII to pAS1 is described in the present invention and pAS1 was deposited in ATCC, Rockville, Md., under Accession No. 39262.

Upon issuance of a patent, these deposits will continue to be maintained for a period of at least 30 years after deposit, five years after the most recent request for a sample, or for the life of the patent, whichever is longer. The deposits shall be available to the Commissioner during pendency and all restraints on availability will be irrevocably removed upon issuance of a patent.

Adapting pKC30 for the Expression of Eukaryotic Genes and the Changeover to pAS1

Figure 1:
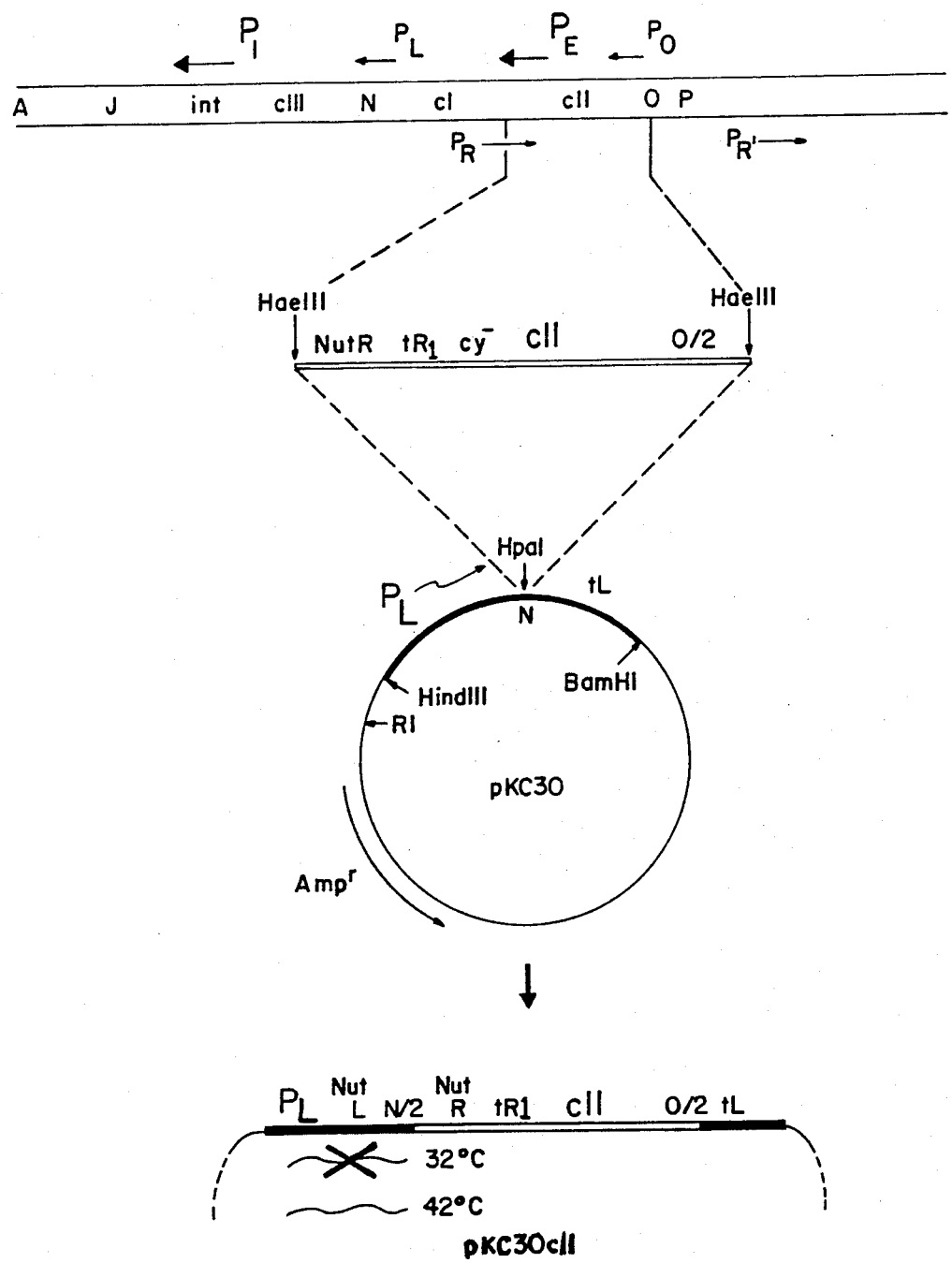
FIG. 1 is a partial genetic map of DNA, pKC30 and pKC30cII. The locations of the positively regulated promoters, $P_E$ and $P_1$, are indicated. These promoters are responsible for the coordinate expression of the phage lysogenic functions, repressor (cI) and integrase (int), respectively. Other major promoters are also shown ($P_R$, $P_L$, $P_O$, $P_R$). Expanded below is the region encompassed by a 1,300-bp HaeIII DNA restriction fragment, which contains the cII gene and several other previously characterized phage regulatory sites. The bottom portion of the figure is a diagram of the construction of the plasmid vector which overproduces cII protein (pKC30cII). The HaeIII restriction fragment was inserted into the single HpaI restriction site which occurs on the plasmid pKC30. This fragment contains the proposed site of recognition for the antitermination function N (NutR), the rho dependent transcription termination site (tR1), the $P_E$ promoter mutation cy3048 (cy−), the cII coding region and the amino-terminal half of the O gene (O/2). The pKC30 plasmid is a derivative of plasmid pBR322 which contains a HindIII-BamHI restriction fragment derived from phage λ inserted between the HindIII and BamHI restriction sites within the tetracycline gene of pBR322. The λ insert contains the promoter signal, $P_L$, another proposed site of N recognition (NutL), the N gene and the strong rho-dependent transcription termination signal, tL. The HpaI restriction site occurs within the N gene coding region. Purified HaeIII fragment (0.1 pmol) and HpaI-cleaved pKC30 plasmid (0.1 pmol) were blunt-end ligated at 15° C. for 14 h and recleaved with HpaI after ligation. This DNA was used to transform a λ lysogen carrying a temperature sensitive mutation (cI857) in its repressor gene. $Amp^r$ recombinants were obtained and screened by size and restriction for the presence of the insert. Recombinants were obtained carrying the insert in both possible orientations. Note that the final pKC30cII construction contained the transcription regulatory sites, NutL, NutR and tR1, preceding the cII gene. Preliminary studies indicated that high-level protein expression required that the lysogen carry a functional N gene which was induced by temperature. This N gene product presumably functions at the Nut sites to antiterminate transcription at tR1.

The plasmid constructed for the expression of genes which do not normally carry regulatory signals for their translation in bacteria is shown in FIG. 2. This vector, pAS1, is related to pKC30cII except that all λ sequences downstream of the cII initiation codon have been deleted. The BamHI site of pBR322 is now fused directly to the cII ATG (FIG. 1). This fusion retains the BamHI site and positions one side of the staggered cut immediately adjacent to the ATG codon permitting ready access to the cII translational regulatory information. The regulatory region comprising the PL through cII ATG region can thus be used to express heterologous proteins. The three bases which are located in the 5' direction relative to the ATG initiation codon are CAT. Thus, these 6 bases comprise a NdeI site, e.g.

```
...cII...C A|T A T G|G A T C C...3'
...cII...G T A T|A C C T A G|G...5'
    NdeI →              ← BamHI
    site                   site
``` and also the three bases located in the 3' direction help to define the BamH1 site as shown above. From the cleavage lines shown for Nde1 and BamHI, it is seen that coding sequences downstream of the PL-cII to ATG regulatory region uniquely defined at the ATG initiation codon which constitutes a unique characterization for the insertion of a gene coding sequence in the present plasmid vector construct of pAS1 and that the unique coding sequence for the polypeptide is not limited to the BamH1 site but may also be carried into the NdeI site. Thus, insertion of a gene coding sequence for a polypeptide into the NdeI site necessarily restores the pL cII regulatory region. Effectively, the BamHI site can readily be replaced or converted to a different site by standard techniques, and thereby the plasmid vector capable of expressing a polypeptide contains in the direction of transcription the following DNA sequences, namely, a pL promoter, a Nut L site, a Nut R site, a tR1 site, and a cII ribosome binding site including a cII initiation codon which further comprises the coding sequence for the polypeptide of interest immediately adjacent the cII translation initiation codon.

Thus, pAS1, unlike pKC30 and pKC30cII, is a general expression vector suitable for expressing prokaryotic or eukaryotic proteins. pAS1 contains all necessary transcription and translation regulatory information, including a translation initiation codon and, hence, can be used to express any coding sequence, such as heterologous proteins, including mature proteins as well as truncated derivatives. pKC30 does not supply the sequence information required for ribosome recognition and translation of gene sequences. Thus, pKC30 can be used only to express bacterial genes which provide their own translation regulatory information. pKC30cII is pKC30 with a fragment from lambda which contains the entire cII gene as well as regions upstream and downstream of the cII gene. At the time of the cloning of cII in pKC30, sequences within the cII-containing fragment which were required for translation had not been identified. Thus, pKC30cII is essentially like pKC30.

In view of the above, the concept of pAS1 is entirely different from pKC30 and pKC30cII. pAS1 was conceived during the course of experiments being carried out for the purpose of studying the cII gene and its expression. In one of these experiments, a mutation which resulted in placement of a Sau3A restriction site immediately downstream of the putative cII ATG was discovered. The availability of this mutant made it possible to adapt further the cII ATG as part of a BamH1 site. This allowed for the first time specified sequences downstream of the cII ATG to be precisely removed and replaced with other sequences. When such other sequences encoding a gene are placed in frame with the cII ATG, it could then be asked whether all the necessary information for their translation had been retained. Since sequences on either side of the ribosome binding site can influence the efficiency of ribosome recognition and translation, e.g., by affecting the folding of the mRNA, it could not be anticipated whether other gene sequences placed in frame and downstream from the cII ATG would be recognized properly by the bacterial translation system. Applicant's first experiments with the *E. coli* lacZ gene, described in the next following section of this specification, provided the answer.

Development of pAS1 was not merely a matter of replacing the cII coding sequence in pKC30cII with another sequence. As noted, pAS1 was derived only after characterization of a particular mutation of the cII gene. Absent availability of such mutant, there was no procedure available when this parent application was filed to excise the cII coding sequence inasmuch as the array of nucleases and synthetic techniques available now were not available at the time applicant's parent invention was made. Furthermore, whether or not the selected region upstream of the cII coding sequence could be used to express a heterologous coding sequence was not predictable. The cII gene is normally expressed from an intercistronic region within a polycistronic message. At the time of applicant's invention, little was known about translation of such intercistronic regions. The effect on ribosome binding and translation of removing sequences upstream and downstream from an intercistronic translation start site, such as the cII translation start site, could not be anticipated. Thus, the expression of a gene fused directly to the ATG initiation codon, i.e., not a fusion comprising N-terminal cII sequences, was surprising. Even less so could expression of a eukaryotic gene to produce a eukaryotic protein be predicted due, for example, to the unpredictability of the effect on ribosome binding and translation of a message for a eukaryotic protein. A further surprise was the extraordinarily high level of expression using pAS1.

Eukaryotic and/or synthetic genes can be adapted and fused to this unique translation initiation signal. It is most important that all fusions between the gene coding sequence and the cII initiation codon maintain the correct translation reading frame. Below, procedures are described for inserting genes into the pAS1 vector. Note that all cloning experiments with pAS1, like those for pKC30, are carried out in a cI+ lysogen in order to maximize stability of the vector. Expression of the cloned gene takes place in the cI$^{ts}$ lysogen using procedures identical to those described above for pKC30.

Cloning and Expression of Genes in pAS1

Direct insertion at the BamHI site. The genes which can be fused directly to the cII initiation codon are those which contain a BamHI, BglII, Sau3A, NdeI, or BclI restriction site at or near their own initiation codon. The necessary restriction site may occur naturally within the gene or be engineered into the gene by recombinant or synthetic techniques. Standard procedures may be used for the cloning, for clone analysis and expression.

Two genes have been cloned and expressed in pAS1 using this technique, the β-galactosidase gene (lacZ) of *E. coli* and the metallothionein II gene from monkey. The lacZ gene was engineered to contain a unique BamHI site near its 5' end, whereas the metallothionein gene naturally contained a BamHI site at its 2nd amino acid codon. In both cases direct BamHI ligation of the gene into pAS1 appropriately positioned the coding sequence in frame with the cII ATG codon. Expression of both genes was controlled entirely by transcriptional and translational signals provided on pAS1. The pAS1 lacZ construction results in high-level expression of β-galactosidase. Similar results were obtained with the monkey metallothionein gene.

Particularity Factors in pAS1 Antitermination

Nut antitermination system, present in both the cII and pAS1, is a system for achieving high level expression of cII protein. cII production was found to be 8–10 times higher in lysogens which provided N as opposed to those which did not. More recent experiments indicate that the N+Nut system leads to increased expression of other genes cloned into pKC30 which do not have terminator signals preceding them.

The phrase "overproduction of the phage regulatory protein cII" is designed to bring out and emphasize that under ordinary conditions cII is not produced in transcriptional activation in amounts necessary to obtain the protein in sufficient amounts to allow for its purification and biochemical analysis. The cloning of the cII gene onto a multicopy plasmid vector requires an efficient transcriptional unit of which the N+Nut is a portion of that unit which is most important. Also important is the lysogen host which adds by a factor of 8–10 the amount of bacterial lysogens utilized as compared to the lack of lysogen host.

One advantage of this system is that a lysogen carrying a temperature sensitive mutation in the cI gene directed transcription can be activated at any time. Induction is accomplished by simply raising the temperature of the cell culture from 32° to 42° C. Thus, cells carrying the vector can be grown to high density at 32° C. without expression of the clone gene and subsequently induced at 42° C. to synthesize the product.

A further advantage of the N+Nut system is that the N expression removes transcriptional polarity, thereby alleviating termination within the $P_L$ transcription unit. This antitermination effect was particularly important for the expression of cII since a transcription termination signal, tR1, positioned immediately upstream of the cII coding region, would interfere.

Additionally, phage λ with promoters and antitermination factors causes the effect in *E. coli* to keep the system lysogenic; i.e., bearing a lysogenic host.

EXAMPLE 1-A

Expression of SV40 Small t Antigen

Unlike the lacZ construction noted ante in this invention, most genes do not contain the restriction information necessary for their direct insertion into the BamHI site of pAS1. Thus, it was additionally necessary to provide greater flexibility for inserting DNA fragments into the vector. This was accomplished by converting the BamHI site of pAS1 into a blunt-ended cloning site. The four base 5'-overhanging end of the BamHI cleavage site can be removed using one bean nuclease, thereby creating a blunt-end cloning site immediately adjacent to the cII initiation codon. Any gene containing any restriction site properly positioned at or near its 5'-end can now be inserted into this vehicle. Blunt-ended fragments can be inserted directly, whereas other restriction fragments must first be made blunt-ended. This is accomplished by either removing the 5' and 3'-overhanging ends with mung bean nuclease (as above) or "filling-in" the 5'-overhanging ends with DNA polymerase. Of course, this procedure still limits the use of pAS1 to those genes which contain appropriate restriction information near their 5'-termini. In order to make the pAS1 system generally applicable to the expression of any gene, a procedure was developed which allows precise placement of a new restriction site at the second codon (or any other codon) of an gene. Creation of this site permits fusion of the gene in-frame to the cII initiation codon of pAS1.

EXAMPLE 1-B

The small t antigen gene of SV40 does not contain an appropriate restriction site at its 5'-end. Using Ba131 exonucleolytic digestion from an upstream restriction site, the first base (G) of the second codon of the small t gene (ATG GAT . . . ) was fused to an upstream, filled-in AvaI restriction site ( . . . CCCGA).

The fusion, ( . . . CCCGA. . . ) recreated the AvaI site precisely at the second codon of the small t gene. Restriction of this vector with AvaI followed by mung bean nuclease digestion produces a blunt-end which was fused in-frame to the blunt-ended BamHI site of pAS1. The resulting vector, pAS1t, expresses authentic SV40 small t antigen entirely from phage regulatory signals. After only a 60-minute induction period, small t antigen represents some 10% of the total cellular protein. Moreover, $^{35}$S-pulse labeling experiments indicate that small t is the major product being synthesized in these bacteria after temperature induction.

I claim:

1. A method of modifying pAS1 which comprises converting the BamHI site into a blunt-ended cloning site.

2. A method of modifying pAS1 which comprises treating the BamHI site of pAS1 and removing the four base 5'-end of said site with mung bean nuclease to form a blunt-end cloning site immediately adjacent to the cII translation initiation codon.

3. A method of modifying pAS1 by filling in the 5'-overhanging ends of the BamHI cleavage site of pAS1 by treatment with DNA polymerase.

4. A plasmid vector capable of expressing a polypeptide comprising a plasmid containing, in the direction of transcription, the following λ DNA sequences: a PL promoter, a Nut L site, a Nut R site, a tR1 site, a cII ribosome binding site including a cII translation initiation codon, and, immediately adjacent to the translation initiation codon, a unique cloning site.

5. The plasmid vector according to claim 4 in which the cloning site is selected from one member of the group consisting of BamHI, BglII, Sau3A, NdeI and BclI.

6. A plasmid vector capable of expressing a polypeptide comprising a plasmid containing in the direction of transcription, the following λ DNA sequences: a PL promoter, a Nut L site, a Nut R site, a tR1 site, and a cII ribosome binding site including a cII translation initiation codon and which further comprises a coding sequence for a polypeptide of interest immediately adjacent to the cII translation initiation codon.

7. A method of modifying a pAS1 vector by inserting a coding sequence in reading frame with the cII translation initation codon.

8. A method of modifying a pAS1 vector by converting the BamHI site of pAS1 into a blunt-ended cloning site comprising the steps of:
  (1) removing the 5'-overhanging end of the BamHI cleavage site to create a blunt-ended cloning site adjacent to the cII translation initiation codon; and,
  (2) inserting a blunt-ended fragment into the pAS1 vector at the blunt-ended cloning site.

9. The method of claim 8 wherein the removal of the overhang in step (1) is accomplished by use of mung bean nuclease.

10. The method of claim 8 wherein the blunt-ended fragment used in step (2) is produced by removing the overhanging end of the fragment with mung bean nuclease.

11. The method of claim 8 wherein the blunt-ended fragment used in step (2) is produced by filling in the 5'-overhanging ends with DNA polymerase.

* * * * *